(12) United States Patent  
Balog

(10) Patent No.: US 8,287,534 B2
(45) Date of Patent: Oct. 16, 2012

(54) LIGHT EMITTING ELECTROSURGICAL SCALPEL

(76) Inventor: Carl Balog, Portland, OR (US)

( * ) Notice: Subject to any disclaimer, the term of this patent is extended or adjusted under 35 U.S.C. 154(b) by 691 days.

(21) Appl. No.: 12/315,973

(22) Filed: Dec. 9, 2008

(65) Prior Publication Data

US 2010/0145333 A1    Jun. 10, 2010

(51) Int. Cl.
*A61B 18/18* (2006.01)

(52) U.S. Cl. .............. 606/42; 606/39; 606/41; 606/45; 606/48

(58) Field of Classification Search .............. 606/42, 606/45–52, 39, 41
See application file for complete search history.

(56) References Cited

U.S. PATENT DOCUMENTS 3,677,262 A * 7/1972 Zukowski ............... 600/120
4,688,569 A * 8/1987 Rabinowitz ............. 606/42

* cited by examiner

*Primary Examiner* — Laura Bouchelle
(74) *Attorney, Agent, or Firm* — Ater Wynne LLP

(57) ABSTRACT

An improved electrosurgical scalpel, with light emission, for generating electrical signals intended for applications to the body of a patient via an electrosurgical electrode is provided. An electrosurgical scalpel includes a handle with a receptacle portion of a conductive member for mounting and retaining an electrode blade, a light source with a power source encapsulated within the handle and a means to direct the light emitted outwardly towards the electrode tip. Operation of a switch on the handle to an on position serves to complete a circuit, activating the light source and, thereby directing light through an opening or upper portion and out from the first end of the handle towards the distal end of the electrode blade.

20 Claims, 8 Drawing Sheets

LIGHT EMITTING ELECTROSURGICAL SCALPEL

DESCRIPTION

Background of the Invention

1. Field of the Invention

Figure 1:
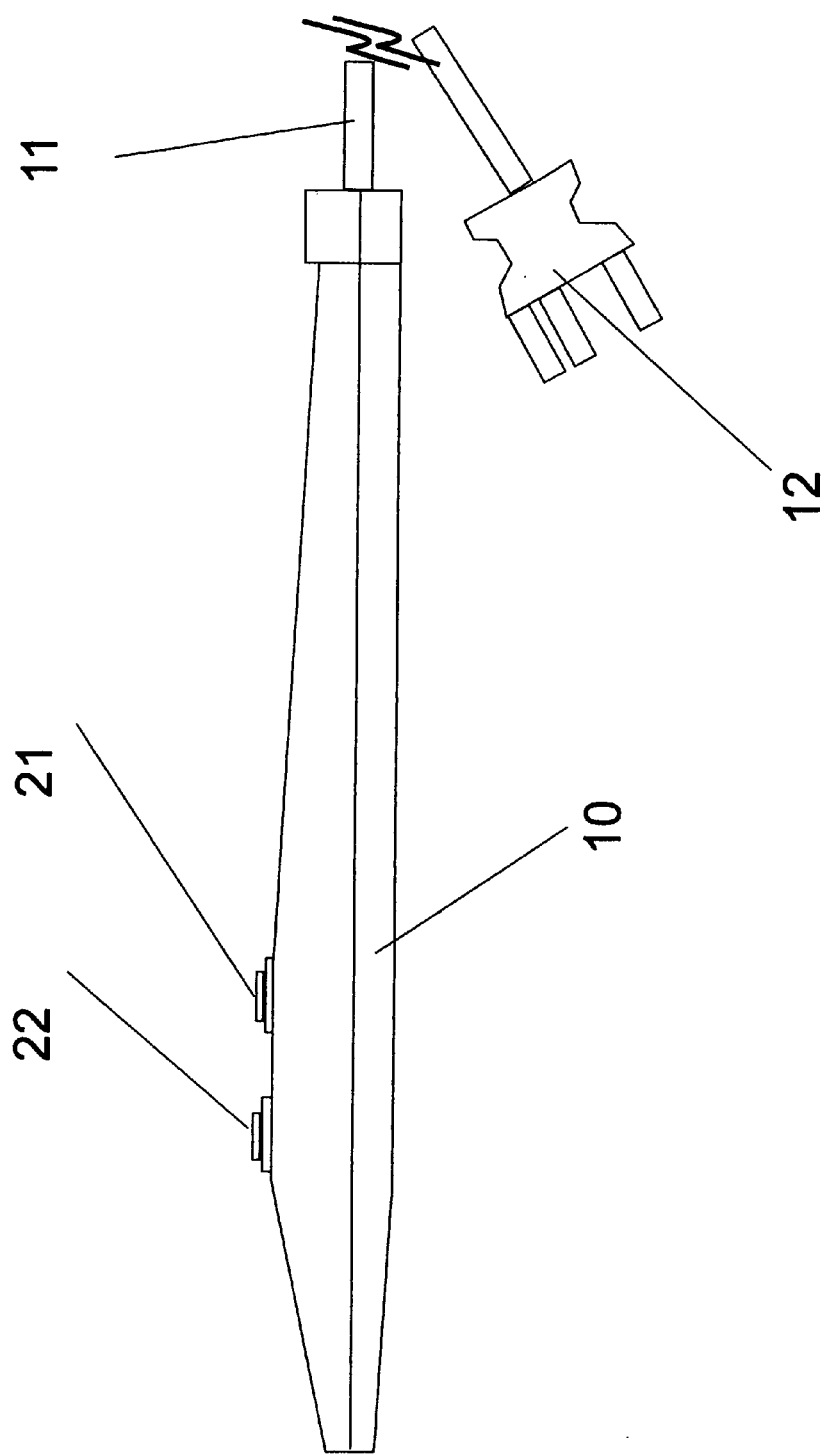
FIG. 1 is a side view of a conventional electrosurgical scalpel.

The present invention relates to diathermic instruments and, more particularly, to a disposable or reusable electrosurgical switch handle and a removable electrode blade that is capable of supplying a high frequency current to a patient.

2. Description of the Prior Art

Various forms of diathermic surgical electrosurgical scalpels have been suggested and utilized in the medical field for a considerable period of time. These instruments have been utilized, for example, to burn or cut tissue. Generally, these instruments have utilized three different signals which are characteristically referred to as cutting signals, coagulation or hemostasis signals and a blend of signals or fulgurating signals which combine both the cutting and coagulation signals. These high frequency or radio frequency signals are generally applied to a patient by an electrode and conducted through the patient's body via a ground path provided by an electrode plate or indifferent plate that is maintained in contact with the patient's body. The application of the signals to the patient is through an electrosurgical electrode which applies the high frequency energy to a concisely concentrated point on the patient's body. The relatively large ground electrode plate provides an area for removing the applied energy without affecting the patient.

As is known, the actual cutting is accomplished by the concentrated application of high frequency electrical energy which effectively destroys the body cells directly beneath the electrosurgical electrode. The hemostasis or coagulation energy signals produce coagulation by the dehydrating or shrinking of the blood vessel walls around a contained clot of coagulated blood. This fusion or uniform coagulation of the blood vessel and its contents effectively seals off the flow of blood. Typically, such coagulation signals or pulses of energy have a dampened sinusoidal wave form.

Activation of the of electrical signals to perform the cutting, coagulation of hermostasis is generally either by activation of a finger operated push contact button, finger operated push contact rocker switch or by foot controlled push contact button switches. The choice of the particular mode of operation of the electrosurgical instrument must frequently be accomplished with a minimum of diversion of the doctor from the site of surgery. In addition, the doctor must be able to maintain his hands on the switching handle that contains the electrosurgical electrode and be able to clearly see the site where the application of the electrode is applied. Finally, it is particularly desirable that the electrosurgical instrument be economically produced, so that it can be disposed after use, thus, insuring a new sterile instrument for each procedure.

It is the intention of the subject invention to provide a highly dependable electrosurgical switching handle, that is compatible with existing signal generators, with the addition of a light emitting source thereby directing light through a portion and out from the first end of the handle towards the distal end of the electrode to provide improved illumination to the concentrated application area around the electrode on the patient's body.

SUMMARY OF THE INVENTION

The present invention provides an electrosurgical switching handle that is compatible with electrosurgical generator units for providing cutting and coagulation in the medical field and a method of manufacturing the same. The handle can be molded from plastic and includes a holding member for appropriate connection of electrical leads to a power supply capable of generating the desired radio frequency or high frequency electrical signals for cutting and coagulation; a holding member for appropriate connection of electrode for the application of electrical signals for cutting and coagulation; a light source, which could take the form of one or more light bulbs, or one or more Light Emitting Diodes (LEDs), and is electrically connected with a power source also encased within the handle such that neither the light bulb nor light power source are able to move relative to the handle; a switch externally accessible on the handle opens and closes the circuit between the light power source and light source to effectively energize and de-energize the light source as desired.

Upon activation of the light by closing the circuit between the light power source and light source, light is directed out from the first end of the handle towards the distal end of the electrode.

In a first preferred embodiment the light power source is one or more batteries, with associated circuit, entirely encapsulated within the handle and isolated and independent from the high frequency electrical signal power supply. Accordingly, when the battery looses the charge, the light source no longer illuminates, however, the electrosurgical switching handle is still used the same as a conventional electrosurgical scalpel. In another preferred embodiment, an alternative, isolated light power source of indefinite life may be connected with the provision of a recharging port which is electrically connected with the light power source. The recharging port is specifically structured for electrical connection with a conventionally available battery recharging device for supplying an electrical recharging current to the light power source. Obviously, in this particular embodiment the light power source would be of a rechargeable type. In another preferred embodiment, the light power source is provided by tapping off available power from the high frequency electrical signal power supply within the handle and is electrically modified to be compatible with the light source and connected to the light source. In another preferred embodiment, an alternative external light power source of indefinite life may be connected with the provision of a connection port which is electrically connected with the light source. The connection port is specifically structured for electrical connection with a conventionally available external power supply device for supplying electrical current to the light source.

With the foregoing in mind it is primary object of the present invention to provide a light emitting electrosurgical scalpel, which is extremely durable yet inexpensive to manufacture.

It is another object of the present invention to provide a light emitting electrosurgical scalpel which is specifically designed to protectively encapsulate a light source, light power supply and electrical conductors within the handle, thereby protecting the contents within the handle from damage due to shock, and maintaining an appropriately ergonomically designed and sized profile for ease of use by the doctors.

It is a further object of the present invention to provide a light emitting electrosurgical scalpel having a handle with a light source and rechargeable battery therein, the handle being provided with a recharging port for recharging the battery.

It is still a further object of the present invention to provide a light emitting electrosurgical scalpel having a light guiding shaft extending from a first end thereof and terminating at a distal end, wherein the electrosurgical scalpel is specifically designed to direct light through a solid light conducting medium from within the handle towards the distal end of the electrode.

It is a further object of the present invention to provide a light emitting electrosurgical scalpel having handle with a light source with electrical connection to an external light power source, the handle being provided with a connection port.

The present invention both to its organization and manner of operation, together with further objects and advantages thereof, may best be understood by reference to the following description, taken in connection with the accompanying drawings and claims.

DETAILED DESCRIPTION OF THE PREFERRED EMBODIMENTS

The following description is provided to enable any person skilled in the art of designing diathermic instruments to make and use the invention and sets forth the best mode contemplated by the inventors of carrying out their invention. Various modifications, however, will remain readily apparent to those skilled in the art, since the operation of the present invention has been described herein to provide an easily manufactured sterile electrosurgical switching handle instrument having component part of an economical nature, so that the instrument is disposable after a single operation on a patient. Thus, the present invention has been optimized to insure the availability of a sterile electrosurgical instrument for every operation.

The electrosurgical switching handle apparatus of the present invention can removably mount an electrode for applying a high frequency electrical signal to biological tissue. The electrode can be powered from a high frequency generator capable of varying the power amplitude of the electrical signals. The doctor can select the desired frequency signal to provide either a cutting or coagulation operative mode. Various forms of high frequency current generators can be utilized along with various forms of electrode blades. With the electrosurgical instrument, a high frequency current will be applied to the tissue by way of an electrode having a relatively small cross section, so as to obtain a high current density at the operation site. Generally, an indifferent electrode which can take the form of a stainless steel plate is operatively connected to the patient and a conductive fluid can be applied to the patient to increase the contact area. It is highly desirable to provide for use with an electrosurgical unit, a disposable sterile switching handle assembly to minimize the possibility of infection.

An example of an electrosurgical switching handle apparatus is depicted in FIG. 1.

Figure 2:
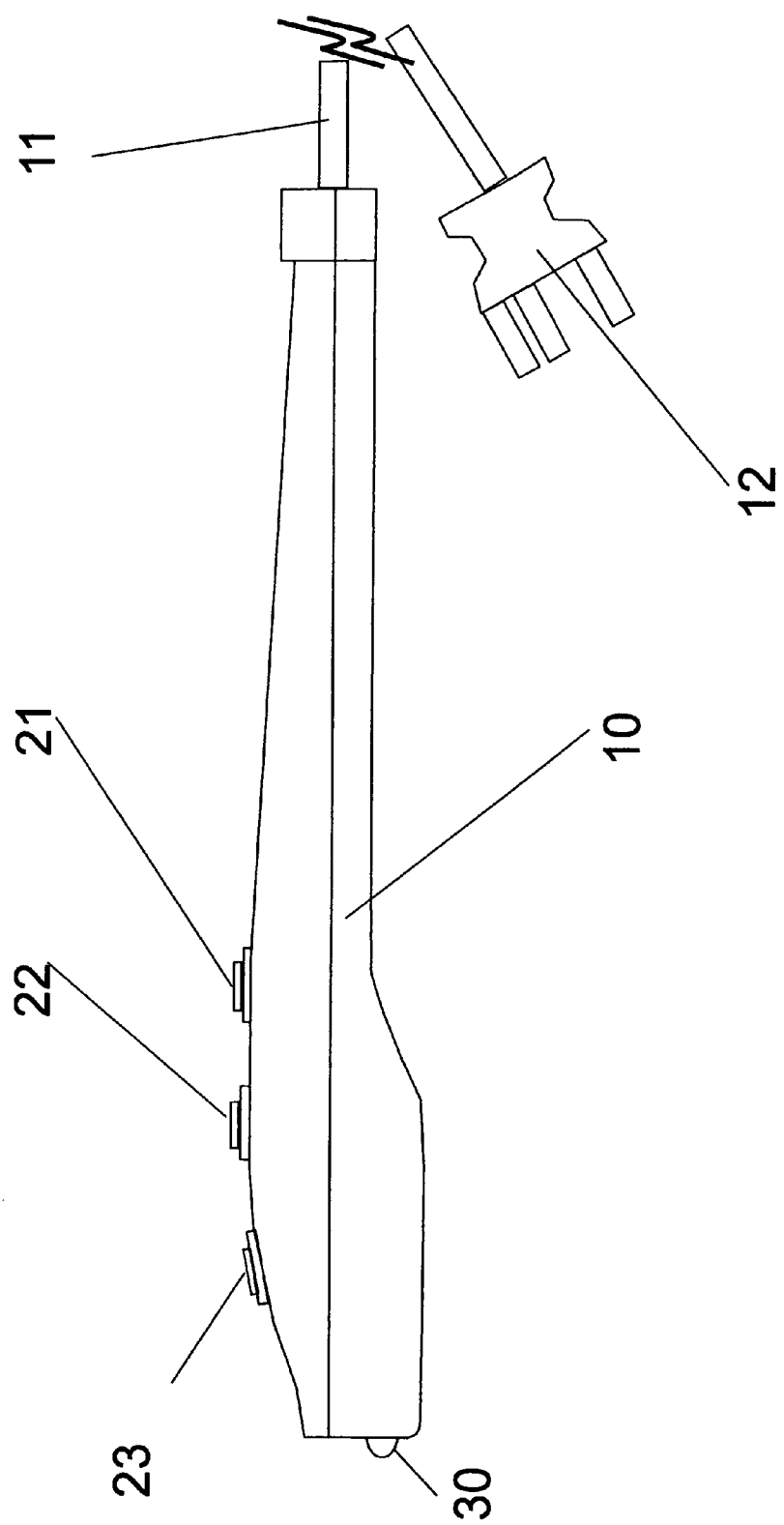
FIG. 2 is a side view of an electrosurgical scalpel according to a first embodiment of the present invention.

As shown in FIG. 2, a electrosurgical scalpel having a light emitting device according to the first embodiment of the present invention comprises a handle 10, electrical leads 11, terminating in a 3-pin plug 12, to a power supply capable of generating the desired radio frequency or high frequency electrical signals for cutting and coagulation, a light emitting device 30, a push button switch to activate cutting signals 22, a push button switch to activate coagulating signals 21 and a push button switch 23 to activate the light source. The handle 10 is made of durable plastic material with the light source projecting light through the front end of the handle.

Figure 3:
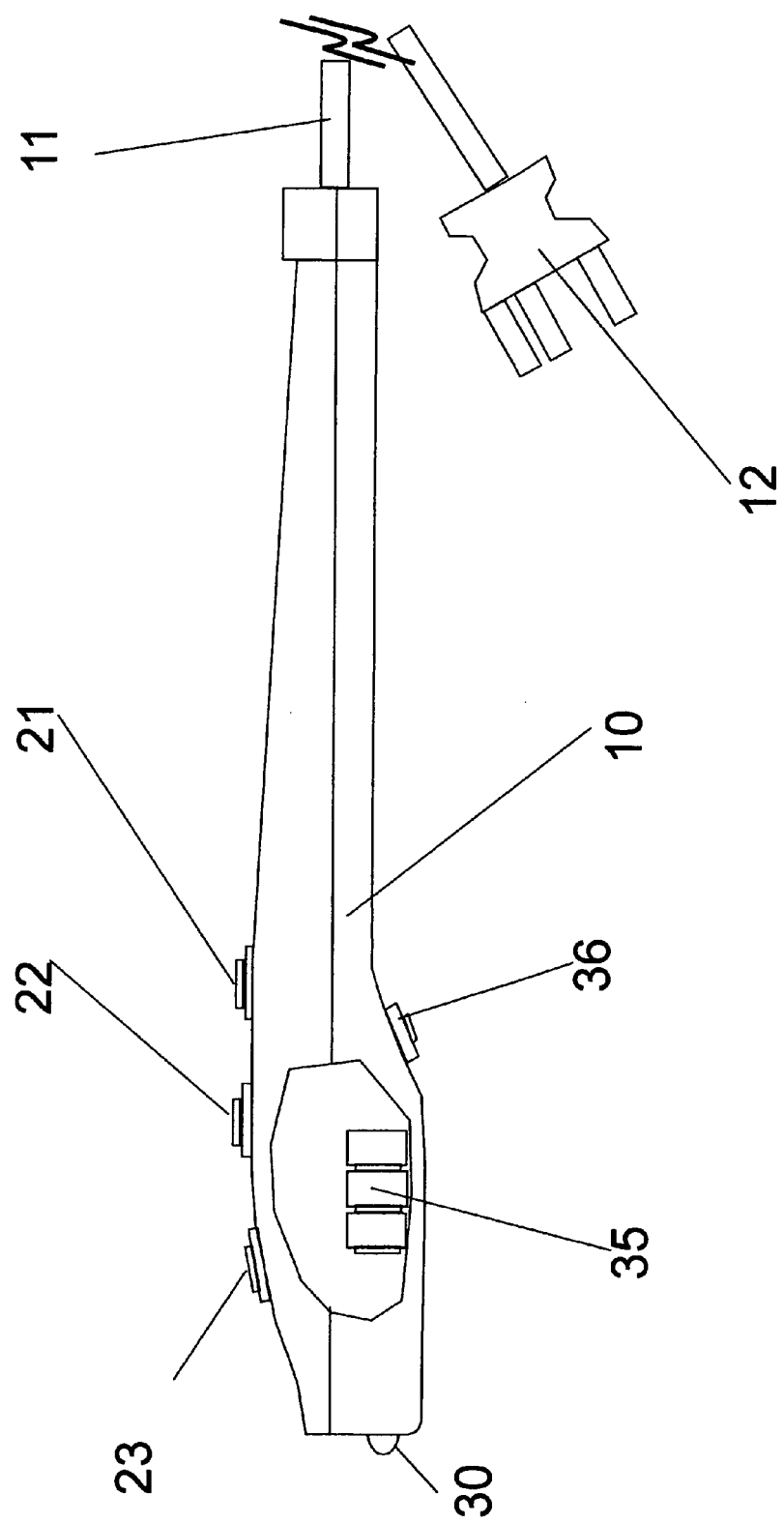
FIG. 3 is a side view of an electrosurgical scalpel, including a cutout view of the area accommodating the power source according to the second embodiment of the present invention.

As shown in FIG. 3, a electrosurgical scalpel having a light emitting device according to the second embodiment of the present invention comprises a handle 10, electrical leads 11, terminating in a 3-pin plug 12, to a power supply capable of generating the desired radio frequency or high frequency electrical signals for cutting and coagulation, a light emitting device 30, a push button switch to activate cutting signals 22, a push button switch to activate coagulating signals 21 and a push button switch 23 to activate the light source. The handle 10 is made of durable plastic material with the light source projecting light through the front end of the handle. Light Power Source Encapsulated within the housing in the form of Rechargeable batteries 35 are mounted within the handle and a recharging port 36 is provisioned within the handle to provide electrical connection with a conventionally available battery recharging device for supplying an electrical recharging current to the battery.

Figure 4:
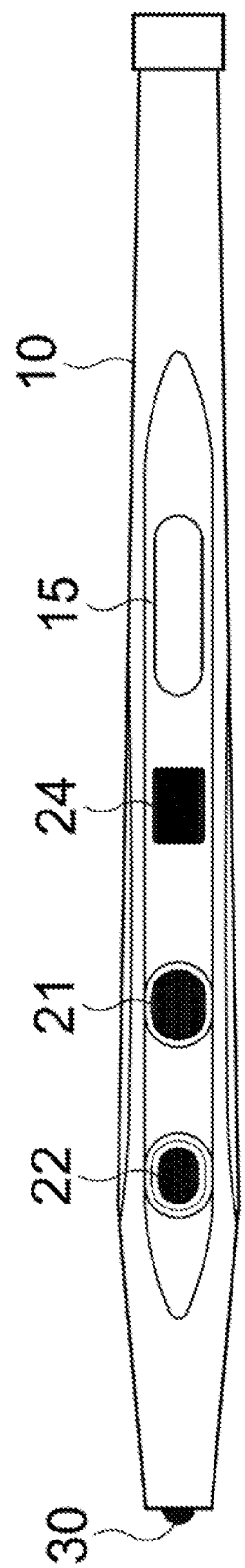
FIG. 4 is a top view, with exemplary dimensions in mm, of an electrosurgical scalpel according to the first embodiment of the present invention, with alternative positioning of switches.

As shown in. FIG. 4, a electrosurgical scalpel having a light emitting device according to the second embodiment of the present invention comprises a handle 10, a light emitting device 30, a push button switch to activate cutting signals 22, a push button switch to activate coagulating signals 21 and a slide switch 24 to activate the light source. The handle 10 is made of durable plastic material with the light source projecting light through the front end of the handle. A molded recess 15 is provided for application of advertising logo and dimensions in mm provided for scaling indication.

Figure 5:
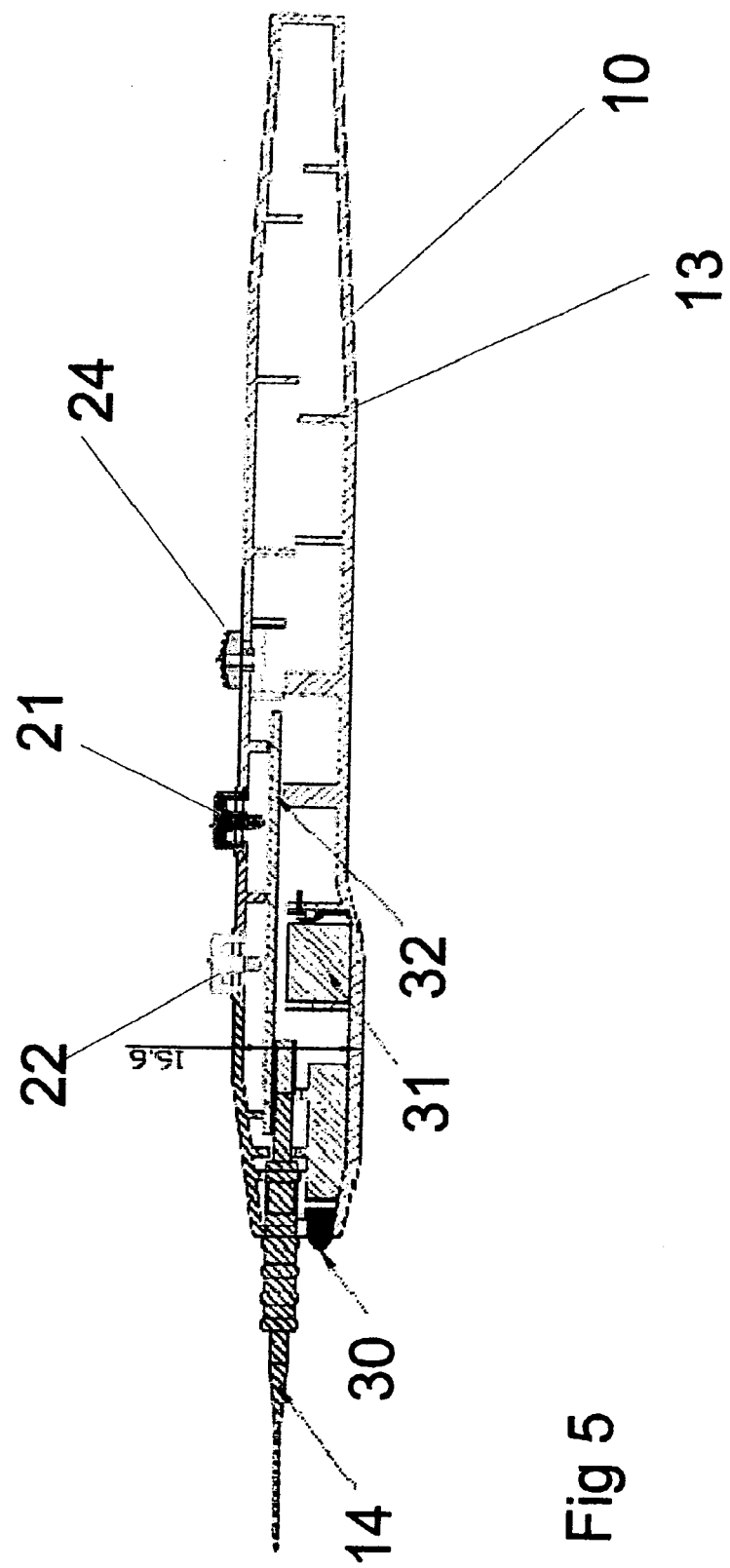
FIG. 5 is a cross-sectional view of an electrosurgical scalpel according to a first embodiment of the present invention, with alternative positioning of switches.

As shown in FIG. 5, a electrosurgical scalpel having a light emitting device according to the second embodiment of the present invention comprises a handle 10, a light emitting device 30, a push button switch to activate cutting signals 22, a push button switch to activate coagulating signals 21 and a slide switch 24 to activate the light source. The handle 10 is made of durable plastic material with the light source projecting light through the front end of the handle. Internal ribs 13 of suitable size and position provide the necessary internal support and guide paths for holding circuit board 32, Light Power Source Encapsulated within the housing in the form of batteries 31, electrode 14, and internal wire connections securely in position.

The electrosurgical switching handle assembly includes housing 10 which can have any desired configuration. In the preferred embodiment, the housing 10 is of a tubular shape and is opened at both ends. One end of the housing has a reduced neck portion for mounting a removable electrode blade 14. Preferably, the housing 10 is formed from an injection moldable plastic. Located in the top of the housing are switch buttons 22, 21, which are individually selected to supply high intensity (cut) or lower intensity (coagulation) signals to the electrode. Adjacent the top portion of the housing 10 is area for appropriate indicia, such as CUT and COAG which can be printed or molded on the exterior of the housing 10 adjacent the protruding button members 22 and 21. Buttons 22, 21 protrude freely down onto the circuit board 32 and the electrode 14. is mounted such that electrical connection is established between the electrode 14 and the circuit board 32.

An additional switch 24, is provisioned within the top of the housing 10, which is a single pole slide switch in this example. Electrical connections are provided by means of wire connections established between the positive side of the batteries 31 to one side of the switch 24, and the other side of the switch 24 to the positive terminal of the light source 30 (in this case an LED), with the return wire connection from the negative terminal of the light source 30 to the negative side of the batteries 31. Adjacent the top portion of the housing 10 is area for appropriate indicia, such as ON and OFF which can be printed or molded on the exterior of the housing 10 adjacent the protruding switch member 24. Switch member 24 protrudes freely down into the housing allowing suitable electrical connection of the wire connections.

Figure 6:
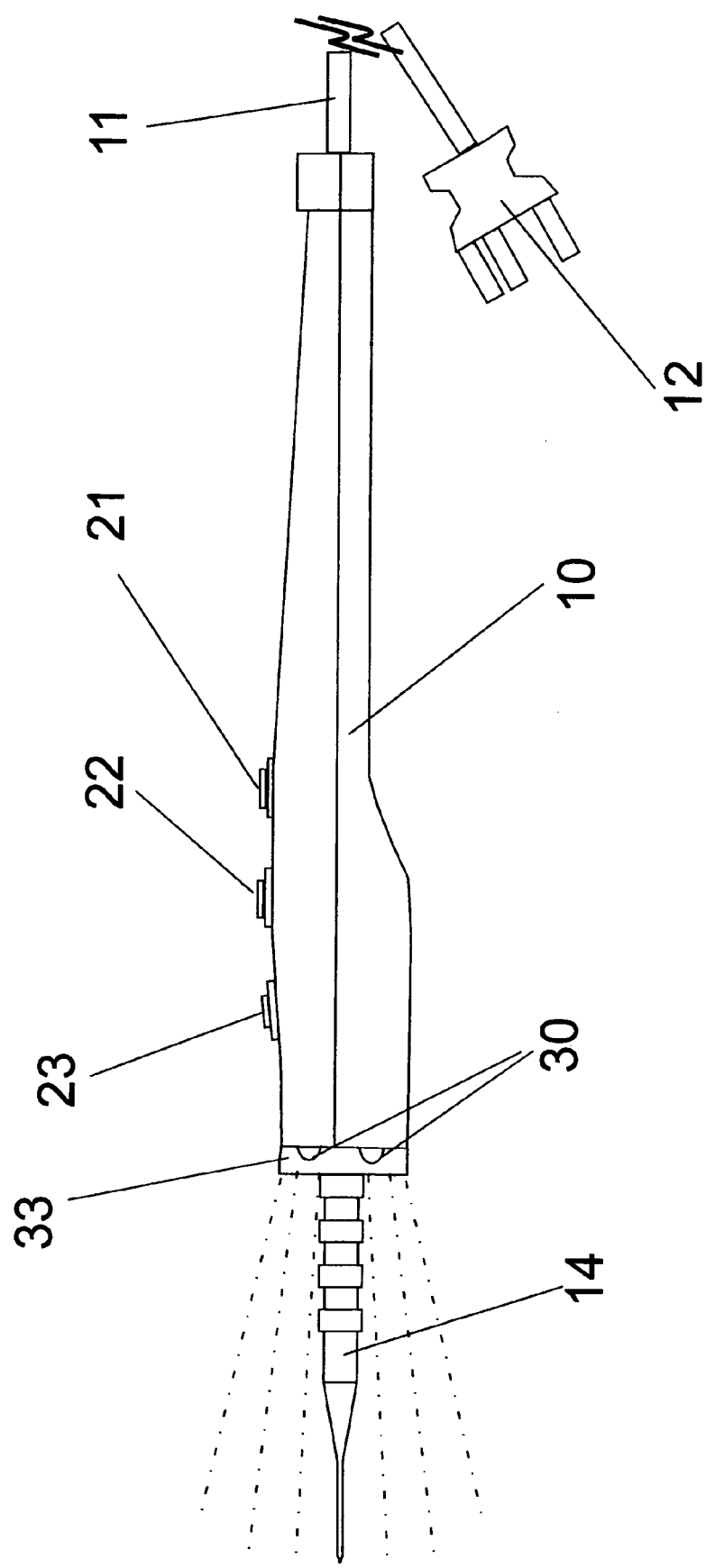
FIG. 6 is a side view of an electrosurgical scalpel, with optical lens arrangement illustrating light emission outwardly towards the electrode tip according to the first embodiment of the present invention.

As shown in FIG. 6, a electrosurgical scalpel having a light emitting device according to the first embodiment of the present invention comprises a handle 10, electrical leads 11, terminating in a 3-pin plug 12, to a power supply capable of generating the desired radio frequency or high frequency electrical signals for cutting and coagulation, a light emitting source comprising two light emitting elements 30, a push button switch to activate cutting signals 22, a push button switch to activate coagulating signals 21 and a push button switch 23 to activate the light source. The handle 10 is made of durable plastic material with the light source projecting light through the front end of the handle. A lens 33 is made of transparent material so that light emitted by the light emitting devices 30 can pass through the front end portion thereof.

Figure 7:
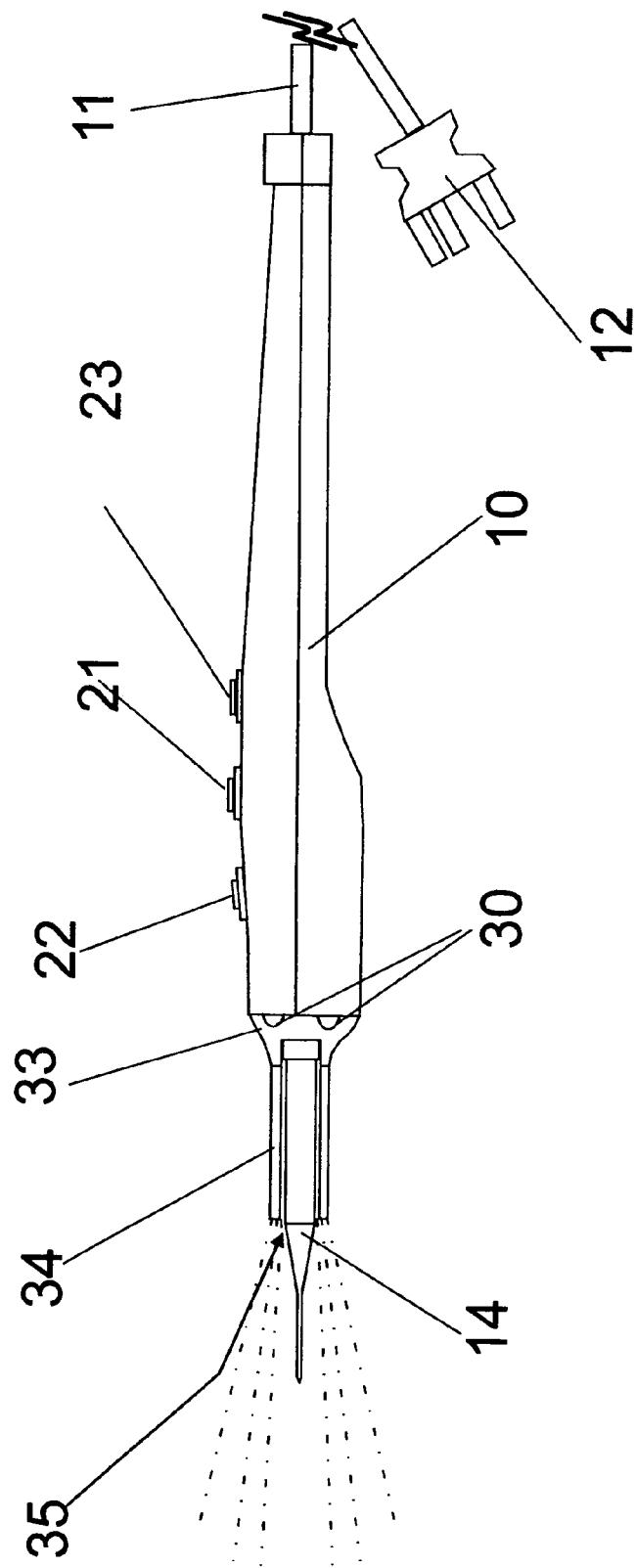
FIG. 7 is a side view of an electrosurgical scalpel, with optical lens arrangement including light guiding sleeve with illustration of light emission outwardly towards the electrode tip according to the first embodiment of the present invention.

As shown in FIG. 7, a electrosurgical scalpel having a light emitting device according to the first embodiment of the present invention comprises a handle 10, electrical leads 11, terminating in a 3-pin plug 12, to a power supply capable of generating the desired radio frequency or high frequency electrical signals for cutting and coagulation, a light emitting source comprising two light emitting elements 30, a push button switch to activate cutting signals 22, a push button switch to activate coagulating signals 21 and a push button switch 23 to activate the light source. The handle 10 is made of durable plastic material with the light source projecting light through the front end of the handle. A lens 33 is made of transparent material so that light emitted by the light emitting devices 30 can pass through the front end portion thereof. The light guiding sleeve 34 is made of transparent plastic material and is a hollow tube of a proper length. The light guiding sleeve 34 has a through hole 35 therein corresponding to the shape of the electrode 14. The electrode 14 is sleeved in the through hole 35 of the light guiding sleeve 34. The rear end of the light guiding sleeve 34 abuts tightly against the front end of the lens 33, and the front end thereof extends to be near the tip of the electrode. Thereby, an electrosurgical scalpel having a light emitting device according to the present invention is formed.

Figure 8:
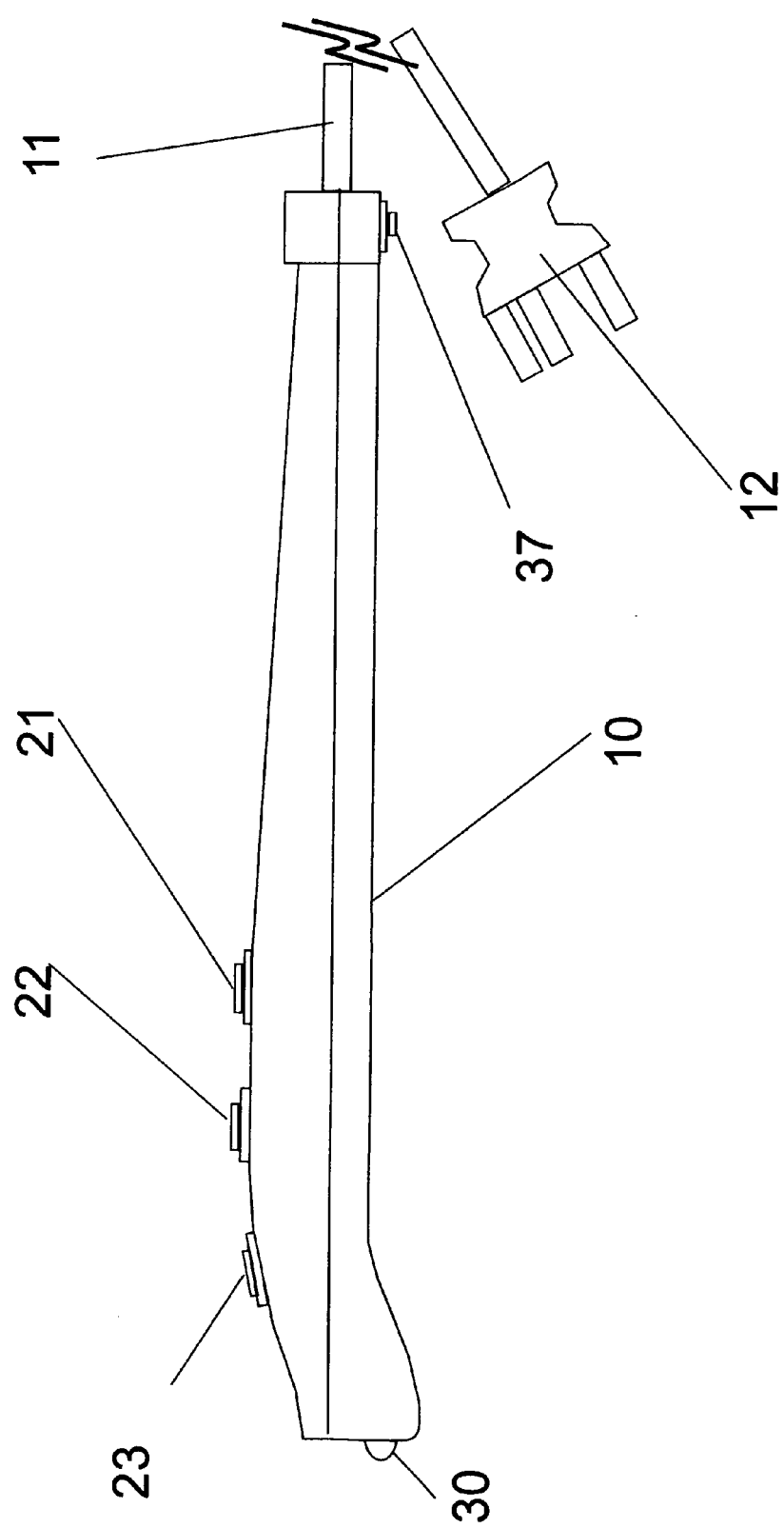
FIG. 8 is a side view of an electrosurgical scalpel, including a connection port to an external light power source according to the first embodiment of the present invention.

As shown in FIG. 8, a electrosurgical scalpel having a light emitting device according to the first embodiment of the present invention comprises a handle 10, electrical leads 11, terminating in a 3-pin plug 12, to a power supply capable of generating the desired radio frequency or high frequency electrical signals for cutting and coagulation, a light emitting device 30, a push button switch to activate cutting signals 22, a push button switch to activate coagulating signals 21 and a push button switch 23 to activate the light source. The handle 10 is made of durable plastic material with the light source projecting light through the front end of the handle. A connection port 37 is provisioned within the handle to provide electrical connection with a conventionally available external power supply for supplying an electric current to the light source, there being no light power source included within the main body of the electrosurgical scalpel device.

Although the present invention has been described with reference to the preferred embodiments thereof, it will be understood that the invention is not limited to the details thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. An electrosurgical instrument for selectively providing electrical energy to an electrode blade for cutting and coagulation, comprising:
    a housing;
    a reduced neck portion at a first end of the housing, the neck portion being configured to receive and retain an electrode blade extending outwardly therefrom;
    a light source disposed within an interior of the housing;
    a light power source encapsulated within the interior of the housing;
    plural user-selectable switches disposed at an exterior of the housing and extending therethrough to the interior of the housing, wherein:
        a first switch of the plural switches is configured, when depressed, to close an electrical circuit and to communicate to the attached electrode blade either of a cutting signal or a coagulating signal, and
        a second switch of the plural switches is coupled in electrical communication with each of the light source and the light power source, wherein the second switch is configured, when actuated, to close an electrical circuit, to communicate an operable electrical signal to the light source, and to cause the light source to illuminate;
    a circuit board disposed within the housing and directly underlying the first switch, the circuit board further being coupled in electrical communication with the electrode blade; and
    an electrically conductive lead comprising:
        a first end disposed within the housing and being coupled in electrical communication with the circuit board; and
        a second end extending outwardly from the housing and being configured for electrically coupling with an external electrosurgical signal generator.

2. The electrosurgical instrument of claim 1, wherein the light source comprises plural light-emitting elements.

3. The electrosurgical instrument of claim 1, wherein a portion of the light source is presented at an exterior of the housing at the first end thereof.

4. The electrosurgical instrument of claim 1, wherein the light source is a light-emitting diode (LED).

5. The electrosurgical instrument of claim 1, wherein the first end of the housing includes a transparent lens configured to allow light from the light source to pass outwardly from the housing through the first end.

6. The electrosurgical instrument of claim 1, wherein either or both of the cutting signal and the coagulating signal comprises one of a radio frequency signal or a high-frequency electrical signal.

7. The electrosurgical instrument of claim 1, wherein:
depressing the first switch causes a portion of the switch within the housing to contact the underlying circuit board and to complete an electrical circuit connecting the electrode blade and the electrosurgical current generator.

8. The electrosurgical instrument of claim 1, further comprising a third switch of the plural switches, wherein the third switch is:
coupled in electrically conductive communication with each of an attached electrode blade and, the electrosurgical current generator;
configured when actuated to close an electrical circuit; and
communicate to the attached electrode blade the other of the cutting signal and the coagulating signal.

9. The electrosurgical instrument of claim 1, further comprising a tubular sleeve formed of a transparent, light-guiding material, wherein:
the sleeve includes a proximal end abutting the first end of the housing and a distal end extending outwardly therefrom;
the attached electrode blade extends through a passageway within the tubular light-guiding sleeve; and
a distal end of the electrode blade extends beyond the distal end of light-guiding sleeve.

10. The electrosurgical instrument of claim 1, wherein causing the light source to illuminate causes light to project outwardly from the first end of the housing and toward a distal end of an attached electrode blade.

11. The electrosurgical instrument of claim 7, wherein:
the light power source comprises a rechargeable battery; and
the housing includes a charging port electrically interconnected with the rechargeable battery, the charging port being disposed at an external surface of the housing, and being configured to electrically couple with an external electrical charging device and to conduct an electrical recharging signal from the charging device to the battery.

12. The electrosurgical instrument of claim 1, wherein the second switch is a single-pole slide switch.

13. An electrosurgical instrument for selectively providing electrical energy to an electrode blade for cutting and coagulation comprising:
a housing, a first end therefore being configured to retain an electrode blade attached to and extending outwardly therefrom;
a light-emitting element mounted within the housing, the light-emitting element being positioned and configured, when illuminated, to directly light outwardly from the first end of the housing;
a connection port disposed at an exterior portion of the housing, the connection port being configured to detachably couple with an external power source;
a first switch means disposed at an exterior portion of the housing, wherein the switch means is:
coupled via an electrically conductive lead with each of the connection port and the light-emitting element, and
user-selectable between each of an open-circuit position and a closed-circuit position, wherein selecting the closed-circuit position completes an electrical circuit between the light-emitting element and the external power source;
a second switch means disposed at an exterior portion of the housing and extending therethrough to an interior of the housing; and
a circuit board disposed within the housing and directly underlying the second switch to be contacted by the second switch when the second switch is depressed, the circuit board further being coupled in electrical communication with the electrode blade; and
an electrically conductive lead comprising:
a first end being coupled in electrical communication with the circuit board; and
a second end extending outwardly from the housing and being configured to electrically couple with an external electrosurgical signal generator.

14. The electrosurgical instrument of claim 13, wherein the external power source and the external electrosurgical signal generator comprise a single power supply coupled with the electrosurgical instrument.

15. The electrosurgical instrument of claim 13, wherein the first end of the housing includes a transparent lens configured to allow light from the light-emitting element to pass outwardly from the housing through the first end.

16. The electrosurgical instrument of claim 13, wherein depressing the second switch causes a portion thereof extending within the housing to:
contact the underlying circuit board;
complete an electrical circuit connecting the electrode blade and the electrosurgical current generator; and
communicate from the electrosurgical current generator to the attached electrode blade either of a cutting signal or a coagulating signal.

17. The electrosurgical instrument of claim 16, further comprising a third switch wherein depressing the third switch causes a portion thereof extending within the housing to:
contact the underlying circuit board;
complete an electrical circuit connecting the electrode blade and the electrosurgical current generator; and
communicate from the electrosurgical current generator to the attached electrode blade the other of an operable cutting signal or an operable coagulating signal
communicate to the attached electrode blade the other of the cutting signal and the coagulating signal.

18. The electrosurgical instrument of claim 16, further comprising a tubular sleeve formed of a transparent, light-guiding material, wherein:
the sleeve includes a proximal end abutting the first end of the housing and a distal end extending outwardly therefrom;
the attached electrode blade extends through a passageway within the tubular light-guiding sleeve; and
a distal end of the electrode blade extends beyond the distal end of light-guiding sleeve.

19. The electrosurgical instrument of claim 13, wherein the housing further includes another light-emitting element disposed therein.

20. The electrosurgical instrument of claim 13, wherein a portion of the first end of the housing retaining the electrode blade is configured as a reduced neck portion having a smaller circumference at a distal end thereof than a corresponding circumference of at least another portion of the housing.

* * * * *

UNITED STATES PATENT AND TRADEMARK OFFICE
CERTIFICATE OF CORRECTION

PATENT NO. : 8,287,534 B2  
APPLICATION NO. : 12/315973  
DATED : October 16, 2012  
INVENTOR(S) : Carl Balog Page 1 of 1

It is certified that error appears in the above-identified patent and that said Letters Patent is hereby corrected as shown below:

Column 7:
   at lines 24-28, replace "an attached electrode blade and,the electrosurgical current generator; configured when actuated to close an electrical circuit; and communicate to the attached electrode blade the other of the cutting signal and the coagulating signal" with --an attached electrode blade and the electrosurgical current generator; and configured when actuated to close an electrical circuit and communicate to the attached electrode blade the other of the cutting signal and the coagulating signal--.

Column 7:
   at line 43, replace "claim 7" with --claim 1--.

Col. 8:
   at lines 46-50, replace "communicate from the electrosurgical current generator to the attached electrode blade the other of an operable cutting signal or an operable coagulating signal communicate to the attached electrode blade the other of the cutting signal and the coagulating signal" with --communicate from the electrosurgical current generator to the attached electrode blade the other of an operable cutting signal or an operable coagulating signal--.

Signed and Sealed this  
Twenty-sixth Day of February, 2013

Teresa Stanek Rea  
*Acting Director of the United States Patent and Trademark Office*